(12) United States Patent
Mantyla et al.

(10) Patent No.: US 11,204,329 B2
(45) Date of Patent: Dec. 21, 2021

(54) METHOD AND APPARATUS OF MEASURING PROPERTIES OF A MOVING SHEET

(71) Applicant: VALMET AUTOMATION OY, Espoo (FI)

(72) Inventors: Markku Mantyla, Kangasala (FI); Jussi Graeffe, Kyröskoski (FI); Pekka Jakkula, Lumijoki (FI)

(73) Assignee: VALMET AUTOMATION OY, Espoo (FI)

( * ) Notice: Subject to any disclaimer, the term of this patent is extended or adjusted under 35 U.S.C. 154(b) by 441 days.

(21) Appl. No.: 16/422,127

(22) Filed: May 24, 2019

(65) Prior Publication Data

US 2019/0369027 A1 Dec. 5, 2019

(30) Foreign Application Priority Data

May 30, 2018 (FI) ...................................... 20185490

(51) Int. Cl.
*G01N 21/86* (2006.01)
*G01V 3/08* (2006.01)
(Continued)

(52) U.S. Cl.
CPC .............. *G01N 21/86* (2013.01); *B65H 7/10* (2013.01); *B65H 7/14* (2013.01); *G01J 5/10* (2013.01);
(Continued)

(58) Field of Classification Search
CPC ................... G01N 21/86; G01N 21/31; G01N 2021/8663; G01N 2021/8645;
(Continued)

(56) References Cited

U.S. PATENT DOCUMENTS

| 4,789,820 A | 12/1988 | Parrent, Jr. et al. |
| 7,982,469 B2 | 7/2011 | Jakkula et al. |

(Continued)

FOREIGN PATENT DOCUMENTS

| EP | 1734361 A1 | 12/2006 |
| FI | 123859 B | 11/2013 |
| WO | 2014/191626 A1 | 12/2014 |

OTHER PUBLICATIONS

Jan. 25, 2019 Search Report issued in Finnish Patent Application No. 20185490.

(Continued)

*Primary Examiner* — David P Porta
*Assistant Examiner* — Gisselle M Gutierrez
(74) *Attorney, Agent, or Firm* — Oliff PLC

(57) ABSTRACT

A method of measuring properties of a moving cellulose, paper or board sheet. A first parameter of a first resonance caused by the moving sheet in a frequency range 1 GHz to 25 GHz of electromagnetic radiation is measured. A second parameter of an electromagnetic signal transmitted between at least a pair of transceiver parts of a transceiver sensor located on opposite sides of the moving sheet through the moving sheet is measured in a frequency range 25 GHz to 1000 GHz. A minimum difference between the frequency ranges related to the first parameter and the second parameter being at least 5 GHz. Both the dry stuff content and the weight of water per unit of area are determined on the basis of the first parameter, the second parameter and available information related to a distance travelled by the electromagnetic signal.

14 Claims, 4 Drawing Sheets

(51) Int. Cl.
*B65H 7/10* (2006.01)
*G01N 21/31* (2006.01)
*G01S 17/02* (2020.01)
*B65H 7/14* (2006.01)
*G01J 5/10* (2006.01)

(52) U.S. Cl.
CPC .............. *G01N 21/31* (2013.01); *G01S 17/02* (2013.01); *G01V 3/08* (2013.01); *G01N 2021/8645* (2013.01); *G01N 2021/8663* (2013.01)

(58) Field of Classification Search
CPC ...... G01N 33/346; G01N 22/02; G01N 22/04; G01V 3/08; G01V 3/12; B65H 7/10; B65H 7/14; B65H 2519/00; B65H 2301/542; B65H 2515/11; B65H 2553/24; B65H 7/125; G01S 17/02; G01S 13/88; G01J 5/10; D21F 7/00; D21G 9/00

USPC ................................................... 250/559.01
See application file for complete search history.

(56) References Cited

U.S. PATENT DOCUMENTS

2003/0150266 A1     8/2003   Dammig et al.
2009/0278552 A1*   11/2009   Jakkula ................ G01N 33/346
                                                               324/633

OTHER PUBLICATIONS

Dec. 17, 2019 Office Action issued in German Patent Application No. 10 2019 114 409.4.

* cited by examiner

METHOD AND APPARATUS OF MEASURING PROPERTIES OF A MOVING SHEET

FIELD

The invention relates to a method and an apparatus of measuring properties of a moving sheet.

BACKGROUND

In paper industry, measurement of properties of a moving sheet are very important. Typically, oven dry weight and weight of water per areal unit and basis weight are of interest.

The basis weight has traditionally been measured using gamma- or beta-rays which are radioactive. The radioactive radiation is dangerous to human health and its use has a very tight legislative control in each country. The use of radioactive material requires a special permission which is difficult to receive. There have been alternative approaches which utilize microwave radiation in these measurements, but they suffer from a distance variation between the sensor parts at the opposite sides of the moving sheet and a temperature dependence, for example. There have been attempts to solve the distance variation by using mechanical constructions without success. Hence, there is a need to improve the measurements.

BRIEF DESCRIPTION

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of an apparatus for measuring properties of a moving sheet;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
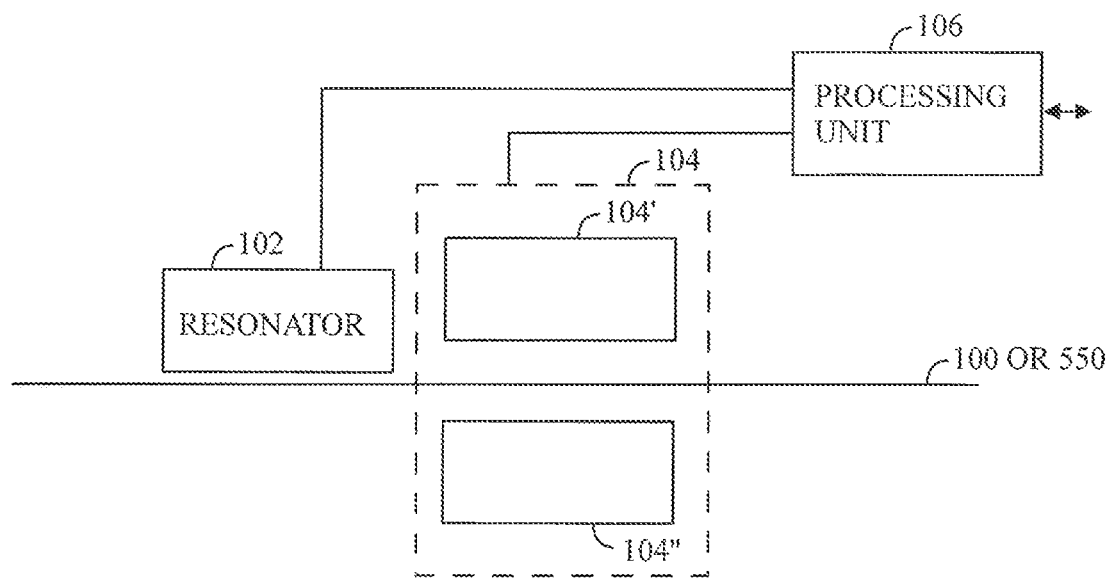

FIG. 1 illustrates an example of an apparatus for measuring properties of a moving sheet. The sheet may be a web manufactured using a paper machine the end product of which is paper or board. The sheet may also be a sheet of cellulose produced in a pulp mill. The apparatus comprises a resonator sensor 102 that measures at least one first parameter of a first resonance caused by the moving sheet 100 in a frequency range 1 GHz to 25 GHz of electromagnetic radiation. The frequency range may be utilized fully or partly. The apparatus also comprises a transceiver sensor 104, which, in turn, comprises at least a pair of transceiver parts 104', 104" located on opposite sides of the moving sheet 100. The transceiver sensor 104 measures at least one second parameter of an electromagnetic signal transmitted between the transceiver parts 104', 104" through the moving sheet 100 in a frequency range 25 GHz to 1000 GHz. The frequency range may be utilized fully or partly.

A minimum difference between the frequency ranges related to the first parameter and the second parameter is at least about 5 GHz. That is, if the first parameters related to the resonance is measured at about 25 GHz, the second parameter related to the transmission measurement must be in a frequency range about 30 GHz to 1000 GHz, for example. Correspondingly, if the second parameter related to the transmission measurement is measured at about 25 GHz, the first parameters related to the resonance must be measured in frequency range 1 GHz to about 20 GHz, for example. On the other hand, if the first parameters related to the resonance is measured at about 10 GHz, the second parameter related to the transmission measurement may be in a frequency range about 25 GHz to 1000 GHz, for example. Still, if the second parameter related to the transmission measurement is performed at about 55 GHz, the first parameters related to the resonance may be measured in frequency range 1 GHz to about 25 GHz, for example. The sensors 102, 104 do not touch the sheet 100 although they are in the vicinity of the sheet 100. The distance between a structure of the sensors 102, 104 and the sheet 100 may be from zero (sensor structure and sheet touch each other) to tens of centimeters, for example. The at least one first parameter and the at least one second parameter are affected by dry stuff content and a weight of water per unit of area of the moving sheet 100 in a different manner due to different effects of dielectric properties of water and/or dry stuff in the moving sheet 100 and to the different kind of measurements. Because of the difference in effects of the dielectric properties of the weight of water and the dry stuff content, the weight of water and the dry stuff content become separable on the basis of at least two different measurements and thus measurable although both affect the measurements. A basis weight BW of the sheet 100 is a combination of the weight of water WW and the dry stuff content OD, i.e. BW=WW+OD. The dry stuff content may also be called an oven dry weight. The basis weight is an areal density of the sheet 100, which refers to its mass per unit of area. The basis weight, in turn, can also be called grammage.

In an embodiment, the resonance may be measured in a range 1 GHz to 5 GHz and the transmission of the electromagnetic signal may be performed in a range 40 GHz to 100 GHz without limiting to these values. Lower frequencies are used for resonance because attenuation would be high, a Q-value would collapse and a pass line error would be high in higher frequencies. The transmission measurement in higher frequencies has higher attenuation and larger phase shifts which results in an accurate and reliable measurement.

Additionally, the apparatus comprises a processing unit 106 that determines both the dry stuff content and the weight of water per unit of area on the basis of the at least one first parameter, the at least one second parameter and available information related to a distance between the transceiver parts 104', 104". If the distance between the transceiver parts 104', 104" changes, a value of the at least one second parameter may also change. When the processing unit 106 has the information related to the distance available, the measurement can be made reliable. If the distance does not change, the information related to it does not need be a variable in the computation performed by the processing unit 106. However, the computation is, in this case, adapted to the constant distance. If the distance varies or may vary, the information related to the distance may be included as a variable in the computation. The distance between the transceiver parts 104', 104" may vary because of mechanical vibration in an industrial environment, for example. In an embodiment, the information related to the distance may be a value of the distance. In an embodiment, the information related to the distance may be a value of a change in the distance.

The measurement principles may be applied in a paper and/or board machine. The measurements may be applied in a pulp drying machine which is similar to a drying section of a paper machine. The drying may be performed using one or more drying cylinders, which are in contact with the sheet 100, and/or one or more airborne dryers which blow heated air to the sheet 100. The drying is mainly based on evaporation in this section/machine.

Figure 2:
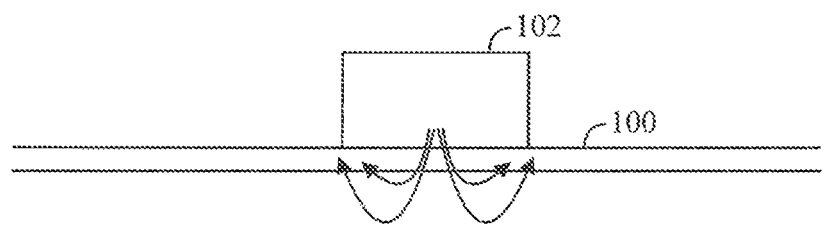
FIG. 2 illustrates an example of a resonator sensor on one side of the sheet.

In an embodiment an example of which is illustrated in FIG. 2, the resonator sensor 102 may locate only on one side of the moving sheet 100 that is measured. The resonator 102 sensor may operate like a part of a waveguide, for example. The resonator sensor 102 does not transmit electromagnetic signals to its environment but it has an electromagnetic interaction with an object, like the sheet 100 close to it (potential leakage of electromagnetic radiation to a far field, which is not a desired feature, cannot be considered transmission). The field lines of an electric near field may be drawn to start from the resonator sensor 102, extend a little outside of the resonator sensor 102 (millimeters, for example) and curve back to the resonator sensor 102. The resonance of the resonator 102 is determined by the dielectric properties of the moving sheet 100. Thus, the weight of water and the dry stuff content in the sheet 100 are able to affect the resonance of the resonator sensor 102.

Figure 3:
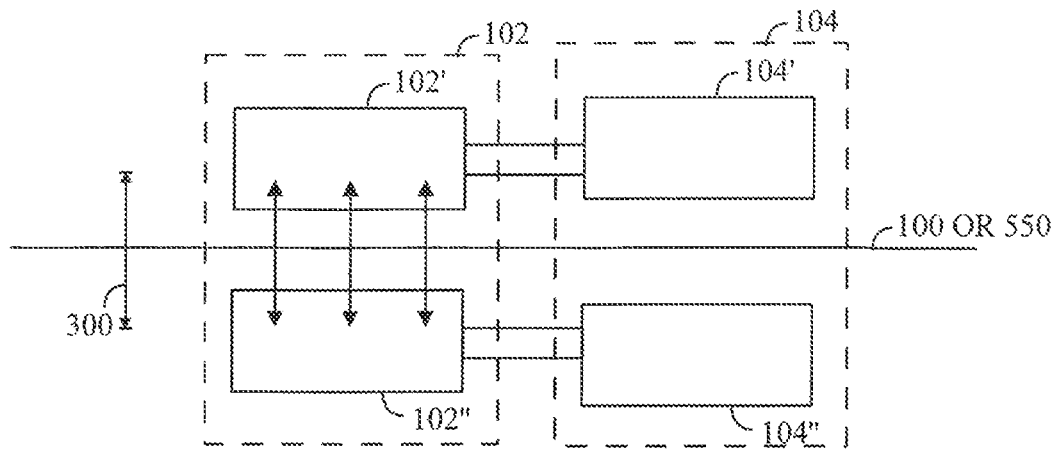
FIG. 3 illustrates an example of a resonator having resonator parts on both sides of the sheet.

In an embodiment an example of which is illustrated in FIG. 3, the resonator sensor 102 may comprise a pair of resonator parts 102', 102" that are located on opposite sides of the moving sheet 100 that is measured. The two open resonator parts 102', 102" are directed towards one another, and between them there is the sheet 100 be measured at the moment of measuring. The resonance of the resonator 102 is determined by the dielectric properties of the moving sheet 100.

In an embodiment, the information related to the distance travelled by the electromagnetic signal between the transceiver parts 104', 104" may be determined by measuring a second resonance of the resonator 102 which has two resonator parts 102', 102". The second resonance has a different frequency from that of the first resonance. The second resonance frequency should be chosen or selected to be more sensitive to an air gap 300 between the resonator parts 102', 102" than to the dry stuff content and the weight of water per unit of area of the moving sheet 100. The electromagnetic field may be at least almost zero at the air gap 300. The parts 102', 102", 104', 104" of the transceiver sensor 104 and the resonator sensor 102 on the same side of the moving sheet 100 are structurally connected such that if the distance between the transceiver parts 102', 102" varies also the distance between the resonator parts 104', 104" varies correspondingly. The structural connection may mean that the parts 102', 102", 104', 104" of the transceiver sensor 104 and the resonator sensor 102 are physically fixed or integrated together. In this manner, their mechanical movement or vibration resemble each other enabling the distance measurement. The structural connection may refer to a mechanical attachment using solid material, for example.

Figure 4:
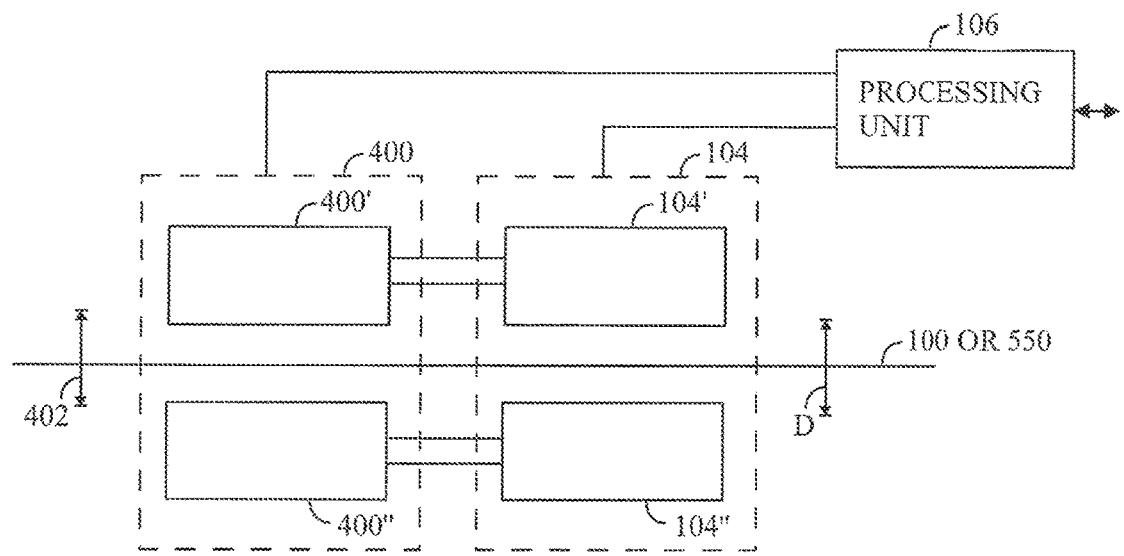
FIG. 4 illustrates an example of the apparatus with a distance measurement device.

In an embodiment an example of which is illustrated in FIG. 4, the apparatus may comprise a distance measurement device 400, which may measure a gap 402 related to the distance D between the pair of the transceiver parts 102', 102". The distance measurement device 400 may comprise an inductive proximity sensor i.e. an Eddy current sensor, which comprises a coil as a first distance measurement device part 400' and a ferromagnet as a second distance measurement device part 400" (or vice versa). If the distance between the distance measurement device parts 400', 400" that are on opposite sides of the moving sheet 100 varies, the inductance of the coil also varies in a corresponding manner. When the distance measurement device parts 400', 400" have a fixed structural connection with the transceiver parts 102', 102", the distance variation between the transceiver parts 102', 102" is deterministically conveyed through the structural connection to a distance variation between the distance measurement device parts 400', 400'. The structural connection may refer to a mechanical attachment using solid material, for example. A person skilled in the art is familiar with the inductive proximity sensors, per se. The distance measurement may also be utilized with the resonance measurement.

In order to perform the computation in the processing unit 106 properly, a number of adjustment measurements with predetermined references may be required. This phase may be called standardization or calibration. In an embodiment, the resonator sensor 102 may measure at least one first parameter of a first resonance caused by at least one adjustment reference 550. That is, adjustment references 550 are measured instead of the moving sheet 100 in this phase.

In an embodiment, the sensors 102, 104 may traverse back and forth the sheet in a transverse direction with respect to a direction of movement of the sheet (movement of sheet may be called machine direction). The adjustment reference(s) may be located beside the sheet 100 such that when or if the sensors 102, 104 cross the edge of the sheet 100 and proceed to an area outside the sheet 100, the adjustment reference(s), which are there, can be measured by the sensors 102, 104.

The transceiver sensor 104 may then transmit electromagnetic signal through the at least one adjustment reference 550 between the pair of the transceiver parts 104', 104".

The processing unit 106, in turn, may determine coefficients of a first function, which defines the water weight on the basis of at least one first parameter and at least one second parameter, as a function of the available information related to the distance between the pair of the transceiver parts 104', 104". Correspondingly, the processing unit 106 may determine coefficients of a second function, which defines the dry weight stuff on the basis of the at least one first parameter and at least one second parameter, as a function of the available information related to the distance between the transceiver parts 104', 104". Any one of the at least one first reference parameter is used only with a unique second reference parameter in determination of the coefficients of the first and second functions. That is, a first reference parameter and a second reference parameter belong together because they are measured from the same adjustment reference 550. Any feature illustrated in FIGS. 1 to 9 can also be applied to reference measurement using the at least one adjustment reference 550. The adjustment reference 550 may be an open space. If the resonator sensor 102 and transceiver sensor 104 traverse cross the sheet 100, the adjustment reference 550 may be measured when the resonator sensor 102 and transceiver sensor 104 are outside the sheet 100 and there is only air within the measurement distance of the resonator sensor 102 or between the resonator sensor parts 102', 102" and between the transceiver parts 104', 104".

The reference adjustment measurement phase may be written in a mathematical form for one distance as follows:

$$R=a*WWr+b*ODr \text{ and } T=c*WWr+d*ODr,$$

where R is a measured resonance, T is a measured transmission, WWr is a known weight of water per unit area, ODr is a known dry stuff content, and a, b, c and d are coefficients. The measured resonance R may refer to a resonance frequency, a change of resonance frequency, a width of a resonance peak, a change of a width of a resonance peak, intensity of a resonance peak, a change of intensity of a resonance peak, a shape of a resonance curve, a change in a shape of a resonance curve, any combination of these or the like, for example. The shape may include the number of high and/or low peaks of the resonance, for example. The measured transmission T may refer to a phase of the electromagnetic signal, a change of the phase of the electromagnetic signal, intensity of the electromagnetic signal, a change of intensity of the electromagnetic signal, any combination of these or the like, for example. By measuring the resonance R and the transmission T, it is possible to separate the variables WW (weight of water per area) and OD (dry stuff content) for the moving sheet 100 and have them in a mathematical form:

$$WW=m*R+n*T \text{ and } OD=u*R+v*T,$$

where m, n, u and v are coefficients determined in a following manner:

$$m=-d/(bc-ad), n=b/(bc-ad), u=c/(bc-ad)$$
$$\text{and } v=-a/(bc-ad).$$

Note that the coefficients a, b, c, d, m, n, u and v actually depend on the distance between the transceiver parts 104', 104" and that is why the adjustment measurements with the adjustment references 550 should be measured using different distances possible or applicable in the measurements of the moving sheet 100, and/or estimated on the basis or a theory and/or simulations.

In an embodiment, the processing unit 106 may determine the dry stuff content on the basis of a resonance frequency or a width of the resonance and a phase of the signal, and the weight of water on the basis of a resonance frequency or a width of the resonance and a phase of the signal, the first and second functions being different from each other.

In an embodiment, the processing unit 106 may determine the dry stuff content on the basis of a resonance frequency shift from a frequency reference or a change in width of the resonance and a phase shift from a phase reference, and the weight of water on the basis of a resonance frequency shift from a frequency reference or a change in width of the resonance and a phase shift from a phase reference.

In an embodiment, the processing unit 106 may determine, with known information related to the distance between the transceiver parts ( ), the dry stuff content (OD) and the weight of water (WW) in at least one of the following manners: $OD=a1*f_r+b1*\phi$ and $WW=c1*f_r+d1*\phi$; $OD=a2*\Delta f_r+b2*\Delta\phi$ and $WW=c2*\Delta f_r+d2*\Delta\phi$; $OD=a3*B_r+b3*\Delta\phi$ and $WW=c3*B_r+d3*\Delta\phi$, where $f_r$ is a resonance frequency, $\phi$ is a phase of received transmission, $\Delta f_r$ is the resonance frequency shift, $\Delta\phi$ is the phase shift of received transmission, $B_r$ is the width of the resonance frequency, and a1, b1, c1, d1, a2, b2, c2, d2 a3, b3, c3 and d3 are predetermined coefficients of the adjustment measurements. The width of the resonance may be measured as a full width at half maximum, for example.

In an embodiment, the processing unit 106 may determine the weight of water of the moving sheet 100 on the basis of the first function that is based on resonance and the dry stuff content of the moving sheet 100 on the basis of the second function that is based on the penetration of the electromagnetic signal through the moving sheet 100 between the transceiver parts 104', 104".

Figure 5:
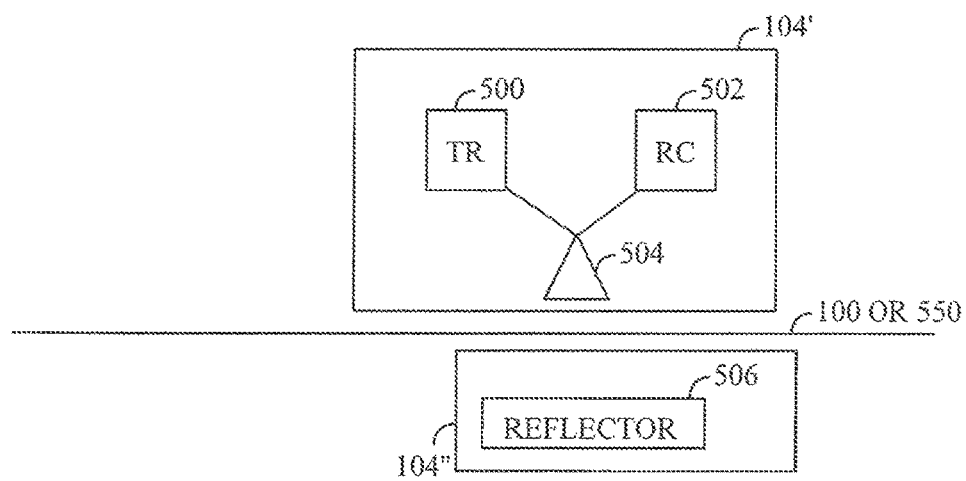
FIG. 5 illustrates an example of the apparatus with a common antenna on one side of the sheet and a reflector on the opposite side.

In an embodiment an example of which is illustrated in FIG. 5, the first transceiver part 104' may comprise a transmitter 500 and a receiver 502 with a common antenna 504, and a second transceiver part 104" comprises a reflector arrangement 506. The transmitter 500 may transmit the signal towards the reflector arrangement 506 through the moving sheet 100, and the reflector arrangement 506 may reflect the signal back to the receiver 502 of the first transceiver part 104' through the sheet 100. The reflector 506 may comprise electrically conductive material. The reflector 506 may comprise a plurality of rows of electrical conductors. The reflector 506 may comprise a piece of flexible flat cable or the like.

Figure 6:
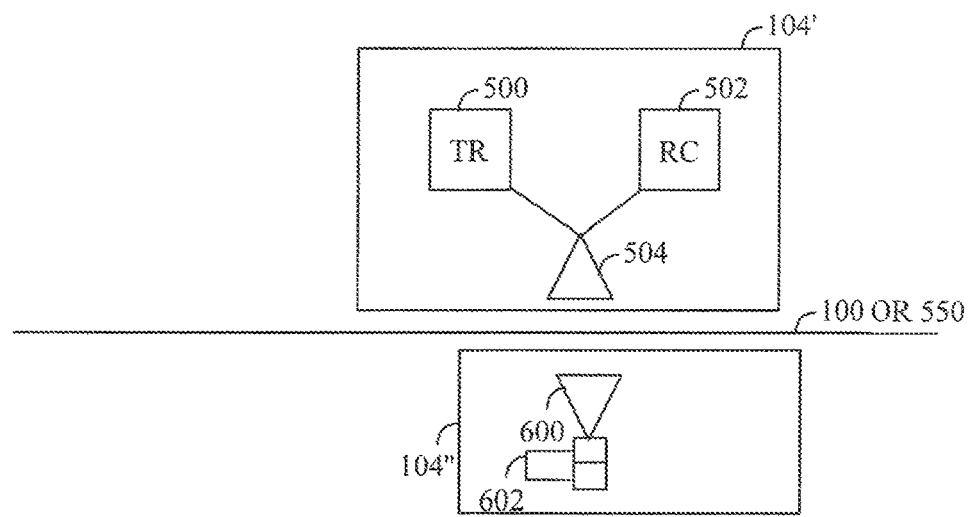
FIG. 6 illustrates an example of the apparatus with a common antenna on one side of the sheet and an antenna and a delay line on the opposite side.

In an embodiment an example of which is illustrated in FIG. 6, the second transceiver part 104" may comprise an antenna 600 and a delay line 602. The transmitter 500 may transmit the signal towards the second transceiver part 104" through the moving sheet 100, the antenna 600 of the second transceiver part 104" may receive the signal, the delay line 602 may delay the signal and the delay line 602 may input the signal back to the antenna 600 of the second transceiver part 104", the antenna 600 transmitting the signal through the moving sheet 100 to the receiver 502. The delay line may comprise a coaxial cable, waveguide or printed circuit board.

Figure 7:
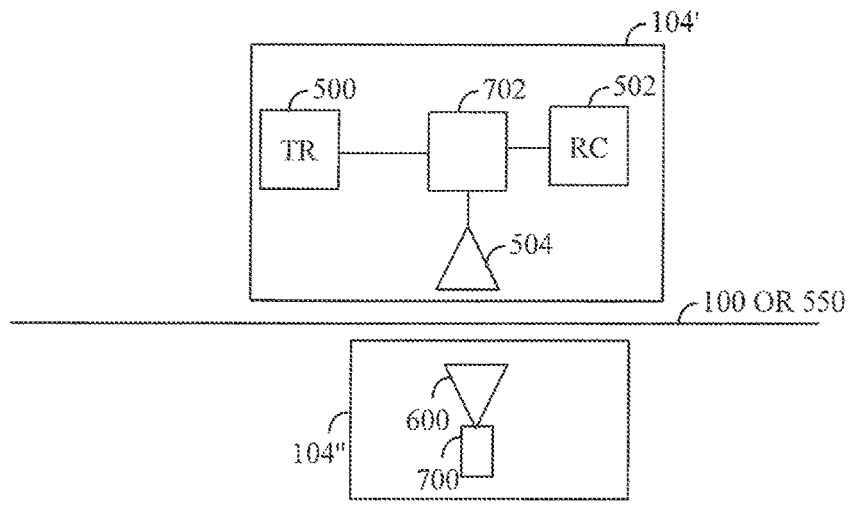
FIG. 7 illustrates an example of the apparatus with a common antenna on one side of the sheet and an antenna and a polarization manipulator on the opposite side.

In an embodiment an example of which is illustrated in FIG. 7, the second transceiver part 104" may comprise an antenna 600 and a polarization manipulator 700. The transmitter 500 may transmit a polarized electromagnetic signal towards the second transceiver part 104" through the moving sheet 100. The antenna 600 of the second transceiver part 104" may receive the polarized signal, and the polarization manipulator 700 may change polarization of the signal. Then the polarization manipulator 700 may input the signal back to the antenna 600 of the second transceiver part 104" for the signal with the manipulated polarization to be transmitted through the moving sheet 100 to the receiver 502. The first transceiver part 104' may have a polarization separator 702 in order to separate output and input signals from each other. The polarization separator 702 may comprise an orto-mode transducer, for example. The signal may be linearly polarized, circularly polarized or elliptically polarized. The manipulated polarization may be orthogonally polarized with respect to an initial polarization. The orthogonal polarization may refer to linear polarizations, which are transverse with respect to each other, or right hand and left hand circular/elliptical polarizations. The second transceiver part 104" may have an amplifier or modulator (not shown in Figures), which may be used to widen a dynamical range of the apparatus. The amplifier or modulator may operate independently without a connection with the first transceiver part 104' although it may also be operationally connected with the first transceiver part 104'. The second transceiver part 104" may have the delay line 602 illustrated in FIG. 6. This embodiment may be made compact.

The ortho-mode transducer (OMT) is a microwave component that can be used in both separation of orthogonally polarized signals from each other in reception/transmission and their combination in transmission/reception.

Figure 8:
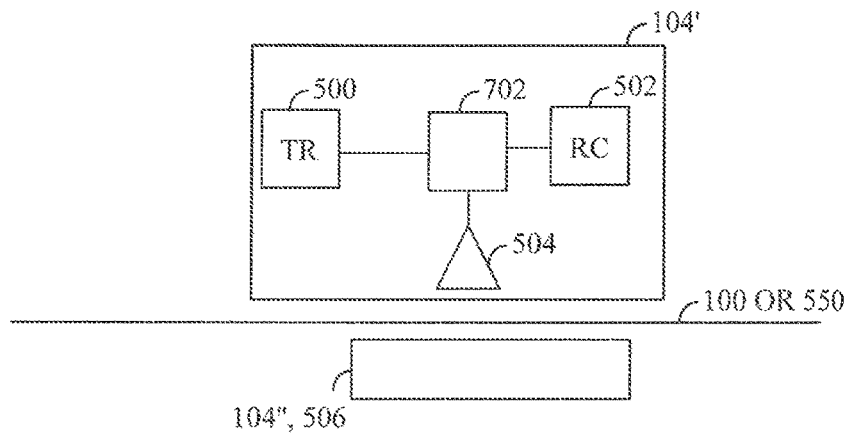
FIG. 8 illustrates an example of the apparatus with a common antenna on one side of the sheet and an antenna and a reflector affecting the polarization on the opposite side.

In an embodiment an example of which is illustrated in FIG. 8, the first transceiver part 104' may output a polarized signal, and a reflector arrangement 506 of the second transceiver part 104" on the opposite side of the moving sheet 100 may convert the signal into an orthogonal polarization with respect to the output polarization in conjunction with the reflection. The first transceiver part 104' may have the polarization separator 702 in order to separate output and input signals from each other on the basis of the orthogonal polarizations.

Figure 9:
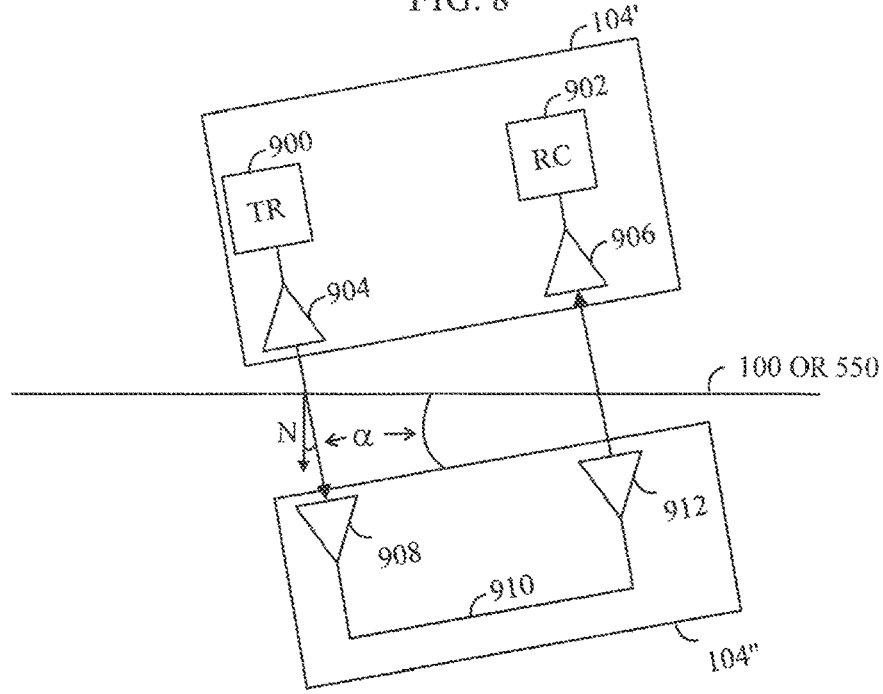
FIG. 9 illustrates an example of the apparatus with separate antennas for transmission and reception on one side of the sheet and separate receiving and transmitting antennas on the opposite side.

In an embodiment an example of which is illustrated in FIG. 9, a first transceiver part 104' may comprise a transmitter 900 and a receiver 902 which are physically separate with their own antennas 904, 906. The second transceiver part 104" may comprise a second side receiving antenna 908 which receives the signal output by the transmitter 900. A signal channel 910, which may guide the received signal from the receiving antenna 908 to a second side transmitting antenna 912, and the second side transmission antenna 912 may then output the signal to the antenna 906 of the receiver 902. The signal channel 910 between the antennas 908, 912 may be a waveguide, a coaxial cable or a printed circuit board, for example In an embodiment an example of which is also illustrated in FIG. 9, a propagation direction of the transmission between the first transceiver part 104' and the second transceiver part 104" is inclined with respect to a normal N of the sheet 100. In an embodiment, the inclination angle α may be between 5° to 45°, for example, without limiting to the range. In an embodiment, the inclination angle α may be between 5° to 25°, for example, without limiting to the range. The first transceiver part 104' and second transceiver part 104" may be inclined structurally (like shown in FIG. 9). The transmission may be directed such that the transmission is inclined without structural inclination. The inclination reduces interference of signals coming from the back side of the moving sheet 100/adjustment reference 550 and the reflection from them which, in turn, reduces disturbance and improves accuracy and reliability of the measurements.

Figure 10:
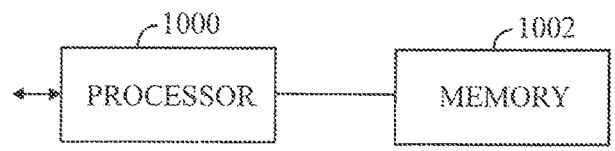
FIG. 10 illustrates an example of the processing unit with at least one processor and memory.

In an embodiment an example of which is also illustrated in FIG. 10, the processing unit 106 may comprise a one or more processors 1000 and one or more memories 1002 including computer program code. The one or more memories 1002 and the computer program code with the one or more processors 1000 may cause the processing unit 106 to perform the determination of both the basis weight and the weight of water in a manner explained above.

The antennas 504, 600, 904, 906, 908, 912 may be horn antennas or flat panel antennas, for example.

In an embodiment, temperature of the sheet may be measured. The temperature measurement may be performed using a pyrometer, an infrared measurement and/or a measurement of air flowing over the sheet 100 in a laminar manner, for example. The measurement of flowing air may be performed with a thermistor or a thermal pair, for example.

Figure 11:
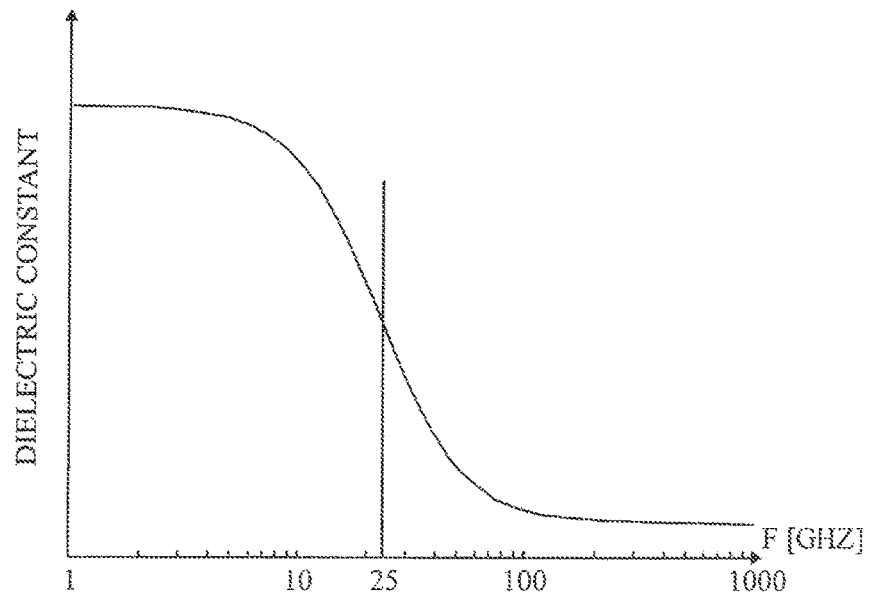
FIG. 11 illustrates an example of dependence between a dielectric constant of water and frequency of electromagnetic radiation.

FIG. 11 illustrates an example of dependence between a dielectric constant of water and a frequency F of electromagnetic radiation in gigahertz. The dielectric constant in y-axis is in arbitrary linear scale but shows that as the frequency of the electromagnetic radiation become higher the dielectric constant becomes smaller.

It is possible to transmit an electromagnetic signal the frequency of which is about 60 GHz through the sheet 100 and measure its attenuation and phase. The measured attenuation and phase may be used to estimate a dry stuff content and water weight of the sheet 100 because phase is more sensitive to the dry stuff and attenuation to the water weight.

Figure 12:
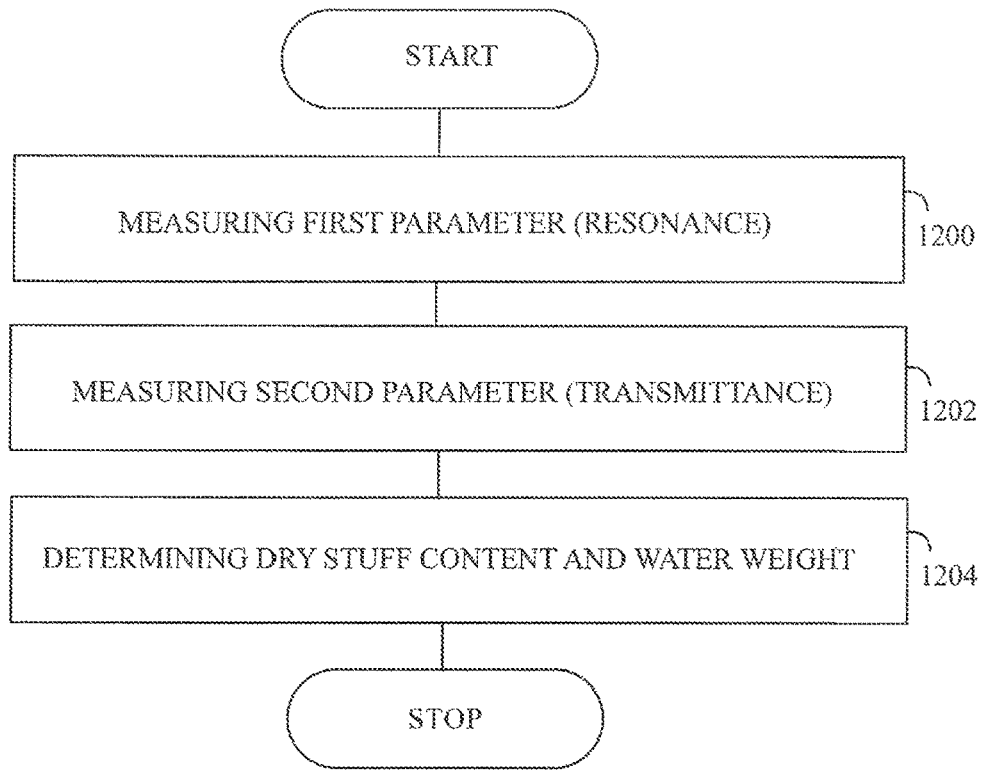
FIG. 12 illustrates of an example of a flow chart of a measuring method.

FIG. 12 is a flow chart of the measurement method. In step 1200 at least one first parameter of a first resonance caused by the moving sheet 100 in a frequency range 1 GHz to 25 GHz of electromagnetic radiation is measured. In step 1202, at least one second parameter of an electromagnetic signal transmitted between at least a pair of transceiver parts 104', 104" of a transceiver sensor 104 located on opposite sides of the moving sheet 100 through the moving sheet 100 in a frequency range 25 GHz to 100 GHz is measured fully or partly. The at least one first parameter and the at least one second parameter are then affected by dry stuff content and a weight of water per unit of area of the moving sheet 100 in a different manner due to dielectric properties of water in the moving sheet 100. In step 1204, both the dry stuff content and the weight of water per unit of area on the basis of the at least one first parameter, the at least one second parameter and available information related to a distance travelled by the electromagnetic signal for measuring the at least one second parameter are determined.

The method shown in FIG. 12 may be implemented as a logic circuit solution or a computer program. The logic circuit may be a sequential state machine the states of which are controlled by the computer program. The computer program causes state transitions specific to the presented method. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

The measurement can effectively be used to control the sheet forming process.

It will be obvious to a person skilled in the art that, as technology advances, the inventive concept can be implemented in various ways. The invention and its embodiments are not limited to the example embodiments described above but may vary within the scope of the claims.

What is claimed is:

1. A method of measuring properties of a moving cellulose, paper or board sheet, the method comprising measuring at least one first parameter of a first resonance caused by the moving sheet in a frequency range 1 GHz to 25 GHz of electromagnetic radiation;

measuring at least one second parameter of an electromagnetic signal transmitted between at least a pair of transceiver parts of a transceiver sensor located on opposite sides of the moving sheet through the moving sheet in a frequency range 25 GHz to 1000 GHz, the at least one first parameter and the at least one second parameter being affected by dry stuff content and a weight of water per unit of area of the moving sheet in a different manner due to dielectric properties of water in the moving sheet, a minimum difference between the frequency ranges related to the first parameter and the second parameter being at least 5 GHz; and determining both the dry stuff content and the weight of water per unit of area on the basis of the at least one first parameter, the at least one second parameter and available information related to a distance travelled by the electromagnetic signal for measuring the at least one second parameter.

2. A method of claim 1, the method further comprising measuring the first resonance in a resonator sensor, which comprises a pair of resonator parts between which the moving sheet is located.

3. A method of claim 2, the method further comprising determining the information related to the distance travelled by the electromagnetic signal by measuring a second resonance of the resonator, which has a different frequency from that of the first resonance; the second resonance frequency is more sensitive to an air gap between the resonator parts than to the dry stuff content and d the weight of water per unit of area of the moving sheet; and the parts of the transceiver sensor and the resonator sensor on the same side of the moving sheet being structurally connected.

4. A method of claim 1, the method further comprising determining the information related to the distance travelled by the electromagnetic signal using an inductive distance sensor, parts of the inductive distance sensor and the parts of the transceiver sensor and the inductive sensor on the same side of the moving sheet being structurally connected.

5. An apparatus for measuring properties of a moving cellulose, paper or board sheet, wherein the apparatus comprises
a resonator sensor configured to measure at least one first parameter of a first resonance caused by the moving sheet in a frequency range 1 GHz to 25 GHz of electromagnetic radiation;
a transceiver sensor comprising at least a pair of transceiver parts located on opposite sides of the moving sheet configured to measure at least one second parameter of an electromagnetic signal transmitted between the transceiver parts through the moving sheet in a frequency range 25 GHz to 1000 GHz, the at least one first parameter and the at least one second parameter being affected by dry stuff content and a weight of water per unit of area of the moving sheet in a different manner due to dielectric properties of water in the moving sheet, a minimum difference between the frequency ranges related to the first parameter and the second parameter being at least 5 GHz;
a processing unit configured to determine both the dry stuff content and the weight of water per unit of area on the basis of the at least one first parameter, the at least one second parameter and available information related to a distance travelled by the electromagnetic signal for measuring the at least one second parameter.

6. The apparatus of claim 5, wherein the resonator sensor comprises a pair of resonator parts that are located on opposite sides of the moving sheet that is measured.

7. The apparatus of claim 5, wherein the apparatus comprises a distance measurement device, which is configured to measure a gap related to the distance travelled by the electromagnetic signal for measuring the at least one second parameter.

8. The apparatus of claim 7, wherein the processing unit is configured to determine the weight of water of the moving sheet on the basis of the first function and the dry stuff content of the moving sheet on the basis of the second function.

9. The apparatus of claim 5, wherein the processing unit is configured to determine the dry stuff content on the basis of a resonance frequency or a width of the resonance and a phase of the signal, and the weight of water on the basis of a resonance frequency or a width of the resonance and a phase of the signal, the first and second functions being different from each other.

10. The apparatus of claim 5, wherein a first transceiver part comprises a transmitter and a receiver with a common antenna, and a second transceiver part comprises a reflector arrangement;
the transmitter is configured to transmit the signal towards the reflector arrangement through the moving sheet, and the reflector arrangement is configured to reflect the signal back to the receiver of the first transceiver part through the sheet.

11. The apparatus of claim 5, wherein a first transceiver part comprises a transmitter and a receiver with a common antenna, and a second transceiver part comprises an antenna and a delay line;
the transmitter is configured to transmit the signal towards the second transceiver part through the moving sheet, the antenna of the second transceiver part is configured to receive the signal, the delay line is configured to delay the signal and the delay line is configured to input the signal back to the antenna of the second transceiver part which is configured to transmit the signal through the moving sheet to the receiver of the first transceiver part.

12. The apparatus of claim 5, wherein first transceiver part is configured to output a polarized signal, a reflector arrangement on the opposite side of the moving sheet is configured to convert the signal into an orthogonal polarization with respect to the output polarization in conjunction with the reflection, and the first transceiver part has a polarization separator in order to separate output and input signals from each other on the basis of the orthogonal polarizations.

13. The apparatus of claim 5, wherein a first transceiver part comprises a transmitter and a receiver which are physically separate with their own antennas, and a second transceiver part comprises a second side receiving antenna which is configured to receive the signal output by the transmitter, a signal channel, which is configured to guide the received signal from the second side receiving antenna to a second side transmission antenna, and the second side transmission antenna is configured to output the signal to the antenna of the receiver.

14. The apparatus of claim 5, wherein a propagation direction of the transmission between the first transceiver part and the second transceiver part is inclined with respect to a normal of the sheet.

* * * * *